United States Patent
Mercep et al.

(10) Patent No.: US 7,232,815 B2
(45) Date of Patent: Jun. 19, 2007

(54) 1-OXA-3-AZA-DIBENZOAZULENES AS INHIBITORS OF TUMOR NECROSIS FACTOR PRODUCTION AND INTERMEDIATES FOR THE PRODUCTION THEREOF

(75) Inventors: Mladen Mercep, Zagreb (HR); Milan Mesic, Zagreb (HR); Dijana Pesic, Sibenik (HR); Iva Benko, Velika Gorica (HR)

(73) Assignee: GlaxoSmithKline, Zagreb d.o.o. (HR)

( * ) Notice: Subject to any disclaimer, the term of this patent is extended or adjusted under 35 U.S.C. 154(b) by 99 days.

(21) Appl. No.: 10/510,620

(22) PCT Filed: Apr. 9, 2003

(86) PCT No.: PCT/HR03/00015

§ 371 (c)(1),
(2), (4) Date: Feb. 25, 2005

(87) PCT Pub. No.: WO03/084964

PCT Pub. Date: Oct. 16, 2003

(65) Prior Publication Data

US 2005/0148576 A1 Jul. 7, 2005

(30) Foreign Application Priority Data

Apr. 10, 2002 (HR) .......................... P 20020304 A

(51) Int. Cl.
- A61K 31/55 (2006.01)
- A61K 31/424 (2006.01)
- C07D 498/22 (2006.01)
- C07D 498/12 (2006.01)

(52) U.S. Cl. ...................... 514/215; 514/375; 548/218; 540/278

(58) Field of Classification Search ................ 544/578; 548/218; 514/215, 375
See application file for complete search history.

(56) References Cited

U.S. PATENT DOCUMENTS

| 3,711,489 | A | 1/1973 | Lombardino |
| 3,838,123 | A | 9/1974 | Viterbo et al. |
| 4,198,421 | A | 4/1980 | Cherkofsky et al. |
| 2005/0130964 | A1* | 6/2005 | Mercep et al. ............ 514/232.8 |
| 2005/0131056 | A1* | 6/2005 | Mercep et al. ............... 514/431 |
| 2005/0137249 | A1* | 6/2005 | Mercep et al. ............... 514/443 |
| 2005/0148576 | A1* | 7/2005 | Mercep et al. ............... 514/215 |
| 2005/0148577 | A1* | 7/2005 | Mercep et al. ............... 514/215 |
| 2005/0171091 | A1* | 8/2005 | Mercep et al. ............... 514/215 |
| 2005/0182126 | A1* | 8/2005 | Mercep et al. ............... 514/431 |
| 2005/0209191 | A1* | 9/2005 | Mercep et al. ................. 514/63 |
| 2005/0227963 | A1* | 10/2005 | Mercep et al. ............... 514/215 |
| 2006/0069149 | A1* | 3/2006 | Mercep et al. ............... 514/443 |
| 2006/0111340 | A1* | 5/2006 | Mercep et al. ............... 514/215 |
| 2006/0241099 | A1* | 10/2006 | Mercep et al. ............... 514/215 |

FOREIGN PATENT DOCUMENTS

| CA | 967573 | 5/1975 |
| HR | 20000310 | 2/2002 |
| JP | 45008611 | 2/1970 |
| WO | WO-01/87890 | 11/2001 |
| WO | WO 91/87890 A1 | 11/2001 |

OTHER PUBLICATIONS

Kimoto and Ohta, Synthesis of 10,11-Dihydro-5H-dibenzo[a,d]-cycloheptene Derivatives, Yakugaku Zasshi, 1967, 87:861-866.
Van Assche and Rutgeerts, Anti-TNF Agents in Crohn's disease, Exp. Opin. Invest. Drugs, 2000, 9: 103-111.
Pfeffer et al., Mice Deficient for the 55kd Tumor Necrosis Factor Receptor Are Resistant to Endotixic Shock, yet Succumb to L. monocytogenes Infection, Cell, 1993, 73:457-467.
Keffer et al., Transgenic mice expressing human tumour necrosis factor: a predictive genetic model of arthritis, EMBO J., 1991, 10:4025-4031.
Georgopoulos et al., Transmembrane TNF Is Sufficient To Induce Localized Tissue Toxicity and Chronic Inflammatory Arthritis in Transgenic Mice, J. Inflamm., 1996, 46:86-97.
Bresnihan, Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.
Mori et al., Attenuation of Collagen-Induced Arthritis in 55-kDa TNF Receptor Type 1 (TNFR1)- lgG1-Treated and TNFR1-Deficient Mice, J. Immunol., 1996, 157:3178-3182.
Elliot et al., Randmoised double-blind comparison of chimeric monoclonal antibody to tumor necrosis factor alpha (cA2) versus placebo in rheumatoid arthritis, The Lancet, 1994, 344:1105-1110.
Carswell et al., An endotoxin-induced serum factor that causes necrosis of tumors, Proc. Natl. Acad. Sci. U.S.A., 1975, 72:3666-3670.
Dinarello, Interleukin-1, Rev. Infect Disease, 1984, 6(1):51-95.
Dinarello, An Update on Human Interleukin-1: From Molecular Biology to Clinical Relevance, J. Clinical Immunology, 1985, 5:287.
Lombardino, Synthesis of Some Novel Tetracyclic Imidazole Derivatives, J Heterocyclic Chem., 1974, 11:17-21.
Cavill, Organic Oxidation Processes, 1955, 4:4426-4429.
Romo et al., Total Synthesis and Immunosuppressive Activity of (-)-Pateamine A and Related Compounds: Implementation of a beta-Lactam-Based Macrocylization, J. Am. Chem. Sco., 1998, 120: 12237-12254.
Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3):1453-1461.
Collier et al., The Abdominal Constriction Response and Its Suppression By Analgesic Drugs in the Mouse, Br. J. Pharmac. Chemother., 1968, 32:295-310.

(Continued)

*Primary Examiner*—Kamal A. Saeed
*Assistant Examiner*—Nyeemah Grazien
(74) *Attorney, Agent, or Firm*—J. Scott Young

(57) ABSTRACT

The present invention relates to derivatives of 1-oxa-3-aza-dibenzoazulene class, to their pharmacologically acceptable salts and solvates, to processes and intermediates for the preparation thereof as well as to their antiinflammatory actions, especially to the inhibition of tumour necrosis factor-α (TNF-α) production and the inhibition of interleukin-1 (IL-1) production as well as to their analgetic action.

14 Claims, No Drawings

OTHER PUBLICATIONS

Fukawa et al., A Method for Evaluating Analgesic Agents in Rats, J. Pharmacol. Meth., 1980, 4:251-259.

Schweizer et al., Combined automated writhing/motility test for testing analgesics, Agents and Actions, 1988, 23:29-31.

Mattioli and Ghia, omega-Dialkylaminoalkyl Ethers of Phenyl-(5-substituted 1-phenyl-1H-pyrazol-4-yl)methanols with Analgesic and Anti-inflammatory Activity, J. Heterocyclic Chem., 1997, 34:963-968.

* cited by examiner

1-OXA-3-AZA-DIBENZOAZULENES AS INHIBITORS OF TUMOR NECROSIS FACTOR PRODUCTION AND INTERMEDIATES FOR THE PRODUCTION THEREOF

TECHNICAL FIELD

The present invention relates to derivatives of 1-oxa-3-aza-dibenzoazulene class, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

PRIOR ART

Hitherto, in the literature derivatives of 1-thia-dibenzoazulenes substituted in 2-position with methyl, methyl-ketone, nitro group or with carboxylic group derivatives (Cagniant P G, *C. R. Hebd. Sceances Acad. Sci.*, 1976, 283:683–686) have been described. Some 1,3-diaza-dibenzoazulene derivatives and salts thereof are known as a novel class of compounds having an antiinflammatory action (U.S. Pat. No. 3,711,489, U.S. Pat. No. 4,198,421 and CA 967, 573). 1-Thia-dibenzoazulene derivatives having alkyloxy substituents in 2-position (WO 01/878990) also possess strong antiinflammatory action.

From dibenzoazulenes of the oxazole class there are known compounds possessing hetero atoms only in the oxazole ring, namely their dihydro derivatives with a 2-phenyl substituent (Schoshichiro K et al., *Yakugaku Zasshi* 1967, 87: 861–866 and JP 45006811) and 2-amino derivatives (ZA 6801411), whereas other completely unsaturated (aromatic) dibenzoazulenes of the oxazole class with a hetero atom (oxygen, sulfur or nitrogen) on the cycloheptane part of the molecule, which represent an object of the present invention, have now been prepared and disclosed for the first time.

According to our knowledge and to available literature data, it has hitherto not been known either that such compounds could possess an antiinflammatory (inhibitors of secretion of TNF-α and IL-1) or analgetic action.

In 1975 TNF-α was defined as a serum factor induced by endotoxin and causing tumour necrosis in vitro and in vivo (Carswell E A et al., *Proc. Natl. Acad. Sci. U.S.A.*, 1975, 72:3666–3670). Besides an antitumour action, TNF-α also possesses numerous other biological actions important in the homeostasis of an organism and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., *Lancet*, 1994, 344:1105–1110) led to an increased interest in finding novel TNF-α inhibitors as possible potent drugs for RA. Rheumatoid arthritis is an autoimmune chronic inflammatory disease characterized by irreversible pathological changes in the joints. Besides in RA, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Evidences for the biological importance of TNF-α were obtained by in vivo experiments in mice, in which mice genes for TNF-α or its receptor were inactivated. Such animals are resistant to collagen-induced arthritis (Mori L et al., *J. Immunol.*, 1996, 157:3178–3182) and to endotoxin-caused shock (Pfeffer K et al., *Cell*, 1993, 73:457–467). In animal experiments where TNF-α level was increased, a chronic inflammatory polyarthritis occured (Georgopoulos S et al., *J. Inflamm.*, 1996, 46:86–97; Keffer J et al., *EMBO J.*, 1991, 10:4025–4031) and its pathological picture was alleviated by inhibitors of TNF-α production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/Wyeth), a fusion protein of the soluble TNF-α receptor, and a chimeric monoclonal human and mouse antibody infliximab (Remicade, Centocor). Besides in RA therapy, etanercept and infliximab are also registered for the therapy of Crohn's disease (*Exp. Opin. Invest. Drugs*, 2000, 9:103).

In RA therapy, besides inhibition of TNF-α secretion, also the inhibition of IL-1 secretion is very important since IL-1 is an important cytokin in cell regulation and immunoregulation as well as in pathophysiological conditions such as inflammation (Dinarello C A et al., *Rev. Infect. Disease*, 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, *J. Clinical Immunology*, 1985, 5:287). Two receptors to which IL-1 may bind are well-known: IL-1RI and IL-1RII. Whereas IL-1RI transfers a signal intracellularly, IL-1RII is situated on the cell surface and does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor (IL-1ra) is present in cells. This protein binds to IL-1RI but does not transfer any signal. However, its potency in stopping the signal transfer is not high and its concentration has to be 500 times higher than that of IL-1 in order to achieve a break in the signal transfer. Recombinant human IL-1ra (Amgen) was clinically tested (Bresnihan B et al., *Arthrit. Rheum.*, 1996, 39:73) and the obtained results indicated an improvement of the clinical picture in 472 RA patients over an placebo. These results indicate the importance of the inhibition of IL-1 action in treating diseases such as RA where IL-1 production is disturbed. Since there exists a synergistic action of TNF-α and IL-1, 1-oxa-3-aza-dibenzoazulenes may be used in treating conditions and diseases related to an enhanced secretion of TNF-α and IL-1.

Inventive Solution

The present invention relates to 1-oxa-3-aza-dibenzoazulenes of the formula I

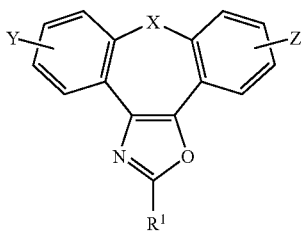

wherein

X may be a hetero atom such as O, S, S(=O), S(=O)$_2$, or NR$^a$, wherein R$^a$ is hydrogen or a protecting group;

Y and Z independently from each other denote one or more identical or different substituents linked to any available carbon atom, and may be hydrogen, halogen, C$_1$–C$_4$ alkyl, C$_2$–C$_4$ alkenyl, C$_2$–C$_4$ alkinyl, halo-C$_1$–C$_4$ alkyl, hydroxy, C$_1$–C$_4$ alkoxy, trifluoromethyl, trifluoromethoxy, C$_1$–C$_4$ alkanoyl, amino, amino-C$_1$–C$_4$ alkyl, N—(C$_1$–C$_4$-alkyl)amino, N,N-di(C$_1$–C$_4$-alkyl)amino, thiol, C$_1$–C$_4$ alkylthio, sulfonyl, C$_1$–C$_4$ alkylsulfonyl, sulfinyl, C$_1$–C$_4$ alkylsulfinyl, carboxy, C$_1$–C$_4$ alkoxycarbonyl, cyano, nitro;

R$^1$ may be hydrogen, C$_1$–C$_7$ alkyl, CHO, (CH$_2$)$_2$COOH, (CH$_2$)$_2$CO$_2$Et, (CH$_2$)$_m$L, wherein m has the meaning of 1 or 3 and L has the meaning of OH or Br; or a substituent of the formula II

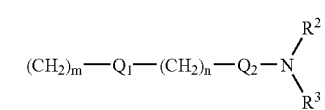

wherein

R$^2$ and R$^3$ simultaneously or independently from each other may be hydrogen, C$_1$–C$_4$ alkyl, aryl or together with N have the meaning of an optionally substituted heterocycle or heteroaryl;

m represents an integer from 1 to 3;
n represents an integer from 0 to 3;
Q$_1$ and Q$_2$ represent, independently from each other, oxygen, sulfur or groups:

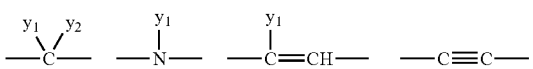

wherein the substituents
y$_1$ and y$_2$ independently from each other may be hydrogen, halogen, C$_1$–C$_4$ alkyl or aryl, hydroxy, C$_1$–C$_4$ alkoxy, C$_1$–C$_4$ alkanoyl, thiol, C$_1$–C$_4$ alkylthio, sulfonyl, C$_1$–C$_4$ alkylsulfonyl, sulfinyl, C$_1$–C$_4$ alkylsulfinyl, cyano, nitro or together form carbonyl or imino group;
as well as to pharmacologically acceptable salts and solvates thereof.

Preferred are compounds: a) wherein X has the meaning of S or O; b) Y and/or Z has the meaning of H, Cl; c) R$^1$ has the meaning of H, CH$_3$, CHO, (CH$_2$)$_2$COOH, (CH$_2$)$_2$CO$_2$Et; d) R$^1$ has the meaning of (CH$_2$)$_m$L; e) symbol m has the meaning of 1 or 3; f) L has the meaning of OH or Br; g) R$^1$ has the meaning of formula II; h) m has the meaning of 1, n has the meaning of 1 or 2, Q$_1$ has the meaning of O, Q$_2$ has the meaning of CH$_2$ and R$^1$ and R$^2$ have the meaning of CH$_3$.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, iso-propyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a C$_1$–C$_4$ alkylene group such as methylene or ethylene.

The term "heteroaryl" relates to groups having the meaning of aromatic and partially aromatic groups of a monocyclic or bicyclic ring with 4 to 12 carbon atoms, at least one of them being a hetero atom such as O, S or N, and the available nitrogen atom or carbon atom is the binding site of the group to the rest of the molecule either via a direct bond or via a C$_1$–C$_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, completely saturated or partly unsaturated heterocyclic groups containing at least one hetero atom such as O, S or N, and the available nitrogen atom or carbon atom is the binding site of the group to the rest of the molecule either via a direct bond or via a C$_1$–C$_4$ alkylene group defined earlier. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably fluorine, chlorine or bromine), hydroxy, $C_1$–$C_4$ alkoxy (preferably methoxy or ethoxy), thiol, $C_1$–$C_4$ alkylthio (preferably methylthio or ethylthio), amino, N—($C_1$–$C_4$) alkylamino (preferably N-methylamino or N-ethylamino), N,N-di($C_1$–$C_4$-alkyl)-amino (preferably dimethylamino or diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl or heterocyclic groups which may be optionally additionally substituted with one or two substituents. The substituents may be halogen (preferably chlorine or fluorine), $C_1$–$C_4$ alkyl (preferably methyl, ethyl or isopropyl), cyano, nitro, hydroxy, $C_1$–$C_4$ alkoxy (preferably methoxy or ethoxy), thiol, $C_1$–$C_4$ alkylthio (preferably methylthio or ethylthio), amino, N—($C_1$–$C_4$) alkylamino (preferably N-methylamino or N-ethylamino), N,N-di($C_1$–$C_4$-alkyl)-amino (preferably N,N-dimethylamino or N,N-diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^2$ and $R^3$ together with N have the meaning of heteroaryl or heterocycle, this means that such heteroaryls or heterocycles have at least one carbon atom replaced by a nitrogen atom through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$–$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may form compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof, including racemates.

The present invention also relates to all possible tautomeric forms of particular compounds of the formula I.

A further object of the present invention relates to the preparation of compounds of the formula I according to processes comprising a) for compounds of the formula I, a cyclisation of a compound of the formula III

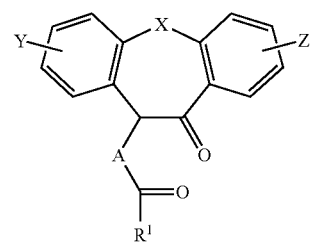

wherein A has the meaning of —O— or —NH—;

b) for compounds of the formula I, wherein $Q_1$ has the meaning of —O—, a reaction of alcohols of the formula IV:

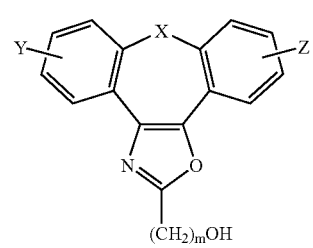

with compounds of the formula V:

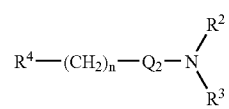

wherein $R^4$ has the meaning of a leaving group;

c) for the compounds of the formula I, wherein $Q_1$ has the meaning of —O—, —NH—, —S— or —C≡C—, a reaction of the compounds of the formula IVa

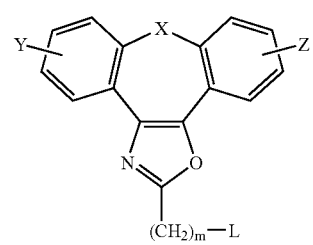

wherein L has the meaning of a leaving group, with compounds of the formula Va

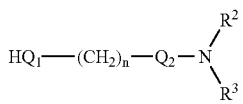

d) for the compounds of the formula I, wherein $Q_1$ has a meaning of a hetero atom —O—, —NH— or —S—,
a reaction of compounds of the formula IVb

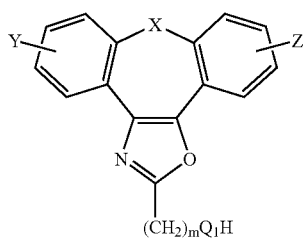

with compounds of the formula V, wherein $R^4$ has the meaning of a leaving group;

e) for compounds of the formula I, wherein $Q_1$ has the meaning of —C≡C—,
a reaction of the compounds of the formula IVb, wherein $Q_1$ has the meaning of carbonyl, with phosphorous ylides.

Preparation Methods:

a) The cyclization of the compounds of the formula III is carried out by methods disclosed for the preparation of analogous compounds. Thus, e.g. compounds of the formula III, wherein A has the meaning of —NH—, may be cyclized by a reaction with $POCl_3$ in organic solvents (preferably benzene or toluene) at boiling temperature during 1 to 5 hours (Lombardino J G, *J. Heterocycl. Chem.*, 1974, 11: 17–21), whereas a cyclization of compounds of the formula III, wherein A has a meaning of —O—, is carried out in the presence of ammonium acetate in acetic acid at boiling temperature during 5 to 10 hours. The obtained tetracyclic products may be isolated by chromatography on a silica gel column or by recrystallization from an appropriate solvent.

The starting substances for the preparation of the compounds of the formula III, ketones of the formula VI,

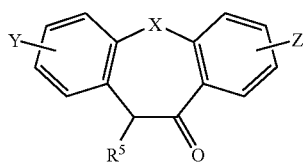

wherein $R^5$ has the meaning of H, are already known or are prepared by methods disclosed for the preparation of analogous compounds. By reacting sodium nitrite in ethanolic hydrochloric acid with a ketone of the formula VI, wherein $R^5$ has the meaning of H, the corresponding oxime is formed, which by the reduction with a metal such as zinc in acetic acid gives an amino compound of the formula VI, wherein $R^5$ has the meaning of $NH_2$ group. A similar reaction course is disclosed in U.S. Pat. No. 4,191,421. By the action of formic acid (Romo D et al., *J. Am. Chem. Soc.*, 1998, 120: 12237–12254) or acid chlorides according to the common protocol, the compounds of the formula III, wherein A has the meaning of —NH— group, are formed.

By the acyloxylation of a corresponding ketone of the formula VI, wherein $R^5$ has the meaning of H atom, with $Pb(OAc)_4$ (Cavill G W K, *Organic Oxidation Processes;* 1955, 4: 4426–4429), the compounds of the formula III, wherein A has the meaning of —O—, are obtained.

b) Compounds of the formula I according to the present process may be prepared by reaction of alcohols of the formula IV and compounds of the formula V, wherein $R^4$ has the meaning of a leaving group, which may be a halogen atom (most frequently bromine, iodine or chlorine) or sulfonyloxy group (most frequently trifluoromethylsulfonyloxy or p-toluenesulfonyloxy). The condensation reaction may be carried out according to methods disclosed for the preparation of analogous compounds (Menozzi G et al., *J. Heterocyclic Chem.*, 1997, 34:963–968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After the treatment of the reaction mixture, the products formed are isolated by recrystallization or chromatography on a silica gel column.

The starting substances, alcohols of the formula IV, may be prepared from the compounds of the formula I, wherein $R^1$ has the meaning of a suitable functional group. Thus e.g. alcohols of the formula IV may be obtained by the reduction of alkanoyl group (e.g. formyl) or alkyloxycarbonyl group (e.g. methyloxycarbonyl or ethyloxycarbonyl) by using metal hydrides such as lithium aluminum hydride or sodium borohydride. Further, alcohols of the formula IV may be prepared by the hydrolysis of the corresponding esters in an alkaline or acidic medium.

The starting compounds of the formula V are already known or are prepared according to methods disclosed for the preparation of analogous compounds.

c) Compounds of the formula I according to the present process may be prepared by reacting compounds of the formula IVa, wherein L has the meaning of a leaving group defined earlier for $R^4$, and compounds of the formula Va, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula IVa (most frequently halides) may be obtained by halogenation (e.g. bromination or chlorination) of alcohols of the formula IV with usual halogenating agents (e.g. hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula Va are already known or are prepared according to methods disclosed for the preparation of analogous compounds.

d) The compounds of the formula I, wherein $Q_1$ has the meaning of —O—, —NH— or —S—, may be prepared by condensation of the compounds of the formula IVb and of compounds of the formula V, wherein $R^4$ has the meaning of a leaving group defined earlier. The reaction may be carried out at reaction conditions disclosed in method b) or by reactions of nucleophilic substitution disclosed in the literature. The starting alcohols, amines and thiols may be obtained by a reaction of water, ammonia or hydrogen sulfide with compounds IVa according to processes disclosed in the literature.

e) The alcohols of the structure IV may be oxidized to corresponding compounds of the formula IVb, wherein $Q_1$ has the meaning of carbonyl and which may further, by reaction with corresponding ylide reagents, result in a prolongation of the chain and in the formation of an alkenyl substituent with carbonyl or ester groups as disclosed in HR patent application No. 20000310.

Besides the above-mentioned reactions, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula IVa with 1-alkyne in an alkaline medium (such as sodium amide in ammonia) the compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and N,N-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. Most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or nitrile group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Craft reaction. By the reduction of the nitro group, an amino group is obtained, which is by diazotizing reaction converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used (Green T W, Wuts P G H, Protective Groups in Organic Synthesis, John Wiley and Sons, 1999) and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially all diseases and conditions induced by excessive TNF-α and IL-1 secretion.

Inhibitors of production of cytokins or inflammation mediators, which are the object of the present invention, or pharmacologically acceptable salts thereof may be used in the production of drugs for the treatment and prophylaxis of any pathological condition or disease induced by excessive unregulated production of cytokins or inflammation mediators, which drugs should contain an effective dose of said inhibitors.

The present invention specifically relates to an effective dose of TNF-α inhibitor, which may be determined by usual methods.

Further, the present invention relates to a pharmaceutical formulation containing an effective non-toxic dosis of the present compounds as well as pharmaceutically acceptable carriers or solvents.

The preparation of pharmaceutical formulations may include blending, granulating, tabletting and dissolving ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. Thus, if a solid carrier is used, these forms may be tablets, hard gelatine capsules, powder or granules that may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of various diseases and pathological inflammatory conditions induced by an excessive unregulated production of cytokins or inflammation mediators, primarily TNF-α. They comprise rheumatoid arthritis, rheumatoid spondylitis, osteoarthritis and other arthritic pathological conditions and diseases, eczemas, psoriasis and other inflammatory skin conditions such as burns induced by UV radiation (sun rays and similar UV sources), inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells In Vitro Human peripheral blood mononuclear cells (PBMC) were prepared from heparinized whole blood after separating PBMC on Ficoll-Paque™Plus (Amersham-Pharmacia). To determine the TNF-α level, $3.5–5 \times 10^4$ cells were cultivated in a total volume of 200 μl for 18 to 24 hours on microtitre plates with a flat bottom (96 wells, Falcon) in RPMI 1640 medium, into which there were added 10% FBS (Fetal Bovine Serum, Biowhittaker) previously inactivated at 54° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, E. coli serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of the stimulus by ELISA procedure (R&D Systems). The percentage of inhibition of TNF-α or IL-1 production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 20 μM or lower concentrations are active.

Determination of TNF-α and IL-1 Secretion in Mouse Peritoneal Macrophages In Vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS portion were added. In order to determine TNF-α secretion, $5 \times 10^4$ cells/well were cultivated in a total volume of 200 μl for 18 to 24 hours on microtitre plates with a flat bottom (96 wells, Falcon) in RPMI 1640 medium, into which 10% fetal bovine serum (FBS, Biowhittaker) inactivated by heat, 100 units/ml of penicillin, 100 mg/ml of streptomycin, 20 mM HEPES and 50 μM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, E. coli serotype 0111:B4, SIGMA) (PC). The effect of the substances upon the TNF-α secretion was investigated after adding them into cultures of cells stimulated with LPS (TS). The TNF-α level in the cell supernatant was determined by ELISA procedure (R&D Systems, Biosource). The IL-1 level was determined in an assay identical to the assay for TNF-α by ELISA procedure (R&D Systems). The percentage of inhibition of TNF-α or IL-1 production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 10 μM or lower concentrations are active.

In Vivo Model of LPS-Induced Excessive TNF-α or IL-1 Secretion in Mice

TNF-α or IL-1 secretion in mice was induced according to the already disclosed method (Badger A M et al., J. Pharmac. Env. Therap., 1996, 279:1453–1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (E. coli serotype 0111:B4, Sigma) in a dosis of 25 μg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production was calculated by the equation:

% inhibition=$[1-(TS-NC)/(PC-NC)]*100$.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier H O J et al., Pharmac. Chemother., 1968, 32:295–310; Fukawa K et al., J. Pharmacol. Meth., 1980, 4:251–259; Schweizer A et al., Agents Actions, 1988, 23:29–31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In Vivo Model of LPS-Induced Shock in Mice

Male Balb/C mice (Charles River, Italy), age 8 to 12 weks, were used. LPS isolated from *Serratie marcessans* (Sigma, L-6136) was diluted in sterile physiological solution. The first LPS injection was administered intradermally in a dosis of 4 μg/mouse. 18 to 24 hours later, LPS was administered i.v. in a dosis of 200 μg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples 7 and 9 show activity in at least two investigated assays though these results only represent an illustration of biological activity of compounds and should not limit the invention in any way.

Preparation Processes with Examples

The present invention is illustrated by the following Examples which are in no way a limitation thereof.

EXAMPLE 1

1-Oxa-8-thia-3-aza-dibenzo[e,h]azulene (1; Table 1)

To a solution of $POCl_3$ (0.137 g, 0.892 mmole) in dry toluene (5 ml), N-(11-oxo-10,11-dihydro-dibenzo[b,f]thiepin-10-yl)-formamide (III; X=S, Y=Z=H. A=NH, $R^1$=H) (0.06 g, 0.223 mmole) dissolved in toluene (10 ml) was added. The reaction mixture was heated under reflux for 2 hours. Then toluene was evaporated to dryness and water was added and it was extracted with ethyl acetate. The organic extract was washed with a saturated $NaHCO_3$ solution and water and dried over anhydrous $Na_2SO_4$. The solvent was evaporated and, after purifying by chromatography on a column, an oily product was isolated.

According to the same process, starting from:
N-(11-oxo-10,11-dihydro-dibenzo[b,f]oxepin-10-yl)-formamide (III; X=O, Y=Z=H, A=NH, $R^1$=H);
N-(11-oxo-10,11-dihydro-dibenzo[b,f]thiepin-10-yl)succinamic acid ethyl ester (III, X=S, Y=Z=H, A=NH, $R^1$=$(CH_2)_2CO_2Et$);
N-(11-oxo-10,11-dihydro-dibenzo[b,f]oxepin-10-yl)succinamic acid ethyl ester (III; X=O, Y=Z=H, A=NH, $R^1$=$(CH_2)_2CO_2Et$), there were prepared the compounds:
1,8-dioxa-3-aza-dibenzo[e,h]azulene;
3-(1-oxa-8-thia-3-aza-dibenzo[e,h]azulene-2-yl)-propionic acid ethyl ester;
3-(1,8-dioxa-3-aza-dibenzo[e,h]azulene-2-yl)-propionic acid ethyl ester;

(Table 1, compounds 2–4)

EXAMPLE 2

2-Methyl-1-oxa-8-thia-3-aza-dibenzo[e,h]azulene (5; Table 1)

To a solution of 11-oxo-10,11-dihydro-dibenzo[b,f]thiepin-10-yl acetic acid ester (III; X=S, Y=Z=H, A=O, $R^1$=$CH_3$) (0.910 g, 3.204 mmole) in acetic acid (25 ml), ammonium acetate (2.47 g, 32.04 mmole) was added. The reaction mixture was heated under reflux for 12 hours and then it was diluted with water (50 ml), neutralized with ammonia and extracted with ethyl acetate. The organic extract was dried over anhydrous $Na_2SO_4$ and evaporated. After purifying by chromatography on a column, a product in the form of a yellow powder was isolated.

According to the same process, starting from:
11-oxo-10,11-dihydro-dibenzo[b,f]oxepin-10-yl acetic acid ester (III; X=O, Y=Z=H, A=O, $R^1$=$CH_3$);
2-chloro-11-oxo-10,11-dihydro-dibenzo[b,f]thiepin-10-yl acetic acid ester (III, X=S, Y=H, Z=2-Cl, A=O, $R^1$=$CH_3$);
2-chloro-11-oxo-10,11-dihydrodibenzo[b,f]oxepin-10-yl acetic acid ester (III; X=O, Y=H, Z=2-Cl, A=O, $R^1$=$CH_3$), there were obtained the compounds:
2-methyl-1,8-dioxa-3-aza-dibenzo[e,h]azulene;
5-chloro-2-methyl-1-oxa-8-thia-3-aza-dibenzo[e,h]azulene in a mixture with 11-chloro-2-methyl-1-oxa-8-thia-3-aza-dibenzo[e,h]azulene;
5-chloro-2-methyl-1,8-dioxa-3-aza-dibenzo[e,h]azulene in a mixture with 11-chloro-2-methyl-1,8-dioxa-3-aza-dibenzo[e,h]azulene (Table 1, compounds 6–10).

EXAMPLE 3

1-Oxa-8-thia-3-aza-dibenzo[e,h]azulene-2-carbaldehyde (11; Table 1)

To a solution of compound 1 (0.334 g, 1.331 mmole) in dry tetrahidrofurane (15 ml) cooled to −78° C., n-BuLi (0.256 g, 3.985 mmole) dissolved in hexane (2.4 ml) was slowly added drop by drop. The reaction mixture was stirred for 15 minutes at the same temperature and then dry dimethylformamide (0.243 g, 3.328 mmole) was added. The reaction mixture was heated to room temperature and stirred for another hour, whereupon water was added thereto and it was extracted with ethyl acetate. The organic extract was dried over anhydrous $Na_2SO_4$ and evaporated. After purifying by chromatography on a column, a product in the form of yellow crystals was isolated.

EXAMPLE 4

3-(1-Oxa-8-thia-3-aza-dibenzo[e,h]azulene-2-yl)-propionic acid (12; Table 1)

Compound 3 (0.280 g, 0.798 mmole) and KOH (0.067 g, 1.197 mmole) were dissolved in ethanol (10 ml) and the reaction mixture was heated under reflux for 2 hours. After the completion of the reaction the solvent was evaporated to a dry residue, water was added and it was extracted with dichloromethane. The aqueous extract was acidified with HCl and the precipitated white crystals were filtered and washed with water.

According to the same process starting from compound 4 3-(1,8-dioxa-3-aza-dibenzo[e,h]azulene-2-yl)-propionic acid (13; Table 1) was prepared.

TABLE 1

Compounds of structure I

| Comp. | X | Y | Z | R[1] | MS (m/z) | $^1$H NMR(ppm, CDCl$_3$) |
|---|---|---|---|---|---|---|
| 1 | S | H | H | H | 252.0 (MH$^+$) | 7.36–7.91(m, 8H); 8.06(s, 1H) |
| 2 | O | H | H | H | 236.1 (MH$^+$) | 7.07–8.02(m, 8H); 8.03(s, 1H) |
| 3 | S | H | H | (CH$_2$)$_2$CO$_2$Et | 352.2 (MH$^+$) | 1.26–1.30(t, 3H); 2.93–2.98(t, 2H); 3.24–3.29(t, 2H); 4.17–4.24(q, 2H); 7.31–7.86(m, 8H) |
| 4 | O | H | H | (CH$_2$)$_2$CO$_2$Et | 358.0 (MNa$^+$) | 1.26–1.30(t, 3H); 2.97–3.02(t, 2H); 3.30–3.35(t, 2H); 4.14–4.22(q, 2H); 7.29–7.85(m, 8H) |
| 5 | S | H | H | CH$_3$ | 266.1 (MH$^+$) | 2.66(s, 3H); 7.33–7.87(m, 8H) |
| 6 | O | H | H | CH$_3$ | 250.0 (MH$^+$) | 2.65(s, 3H); 7.19–7.79(m, 8H) |
| 7 | S | 5-Cl | H | CH$_3$ | 300.1 (MH$^+$) | 2.68(s, 3H); 7.31–7.88(m, 7H) |
| 8 | S | H | 11-Cl | CH$_3$ | 300.1 (MH$^+$) | 2.68(s, 3H); 7.30–7.87(m, 7H) |
| 9 | O | 5-Cl | H | CH$_3$ | 284.2 (MH$^+$) | 2.58(s, 3H); 7.11–7.75(m, 7H) |
| 10 | O | H | 11-Cl | CH$_3$ | 284.2 (MH$^+$) | 2.59(s, 3H); 7.12–7.72(m, 7H) |
| 11 | S | H | H | CHO | | 7.15–7.97(m, 8H); 9.91(s, 1H) |
| 12 | S | H | H | (CH$_2$)$_2$CO$_2$H | 324.0 (MH$^+$) | 3.02–3.07(t, 2H); 3.29–3.33(t, 2H); 7.33–7.87(m, 8H) |
| 13 | O | H | H | (CH$_2$)$_2$CO$_2$H | 308.1 (MH$^+$) | |

EXAMPLE 5

(1-Oxa-8-thia-3-aza-dibenzo[e,h]azulene-2-yl)-methanol (14; Table 2)

To a solution of compound 11 (0.081 g, 0.290 mmole) in methanol (5 ml), NaBH$_4$ (0.016 g, 0.435 mmole) was slowly added. The reaction mixture was stirred at room temperature for 15 minutes and then neutralized with acetic acid. The solvent was evaporated to a dry residue, a saturated NaHCO$_3$ solution was added and it was extracted with dichloromethane. The organic extract was dried over anhydrous Na$_2$SO$_4$ and evaporated. After purifying by chromatography on a column, a product in the form of a light yellow powder was isolated.

According to the same process, starting from esters 3–4 there were prepared the alcohols:
3-(1-oxa-8-thia-3-aza-dibenzo[e,h]azulene-2-yl)-propane-1-ol;
3-(1,8-dioxa-3-aza-dibenzo[e,h]azulene-2-yl)-propane-1-ol (Table 2, compounds 15–16).

EXAMPLE 6

2-Bromomethyl-1-oxa-8-thia-3-aza-dibenzo[e,h]azulene (17; Table 2)

To a solution of compound 5 (0.110 g, 0.415 mmole) in tetrachloromethane (5 ml), N-bromosuccinimide (0.259 g, 1.453 mmole) and a catalytic amount of (PhCO)$_2$O$_2$ were added. The reaction mixture was heated at 77° C. for 3 hours, whereupon it was cooled and the precipitated succinimide was filtered, the solvent was evaporated to a dry residue, water was added thereto and it was extracted with dichloromethane. The organic extract was dried over anhydrous Na$_2$SO$_4$. The solvent was evaporated and after purifying by chromatography on a column, a compound in the form of a yellow powder was isolated.

According to the same process, starting from compounds 6–10 there were prepared bromo derivatives:

2-bromomethyl-1,8-dioxa-3-aza-dibenzo[e,h]azulene;

2-bromomethyl-5-chloro-1-oxa-8-thia-3-aza-dibenzo[e,h]azulene;

2-bromomethyl-11-chloro-1-oxa-8-thia-3-aza-dibenzo[e,h]azulene;

2-bromomethyl-5-chloro-1,8-dioxa-3-aza-dibenzo[e,h]azulene;

2-bromomethyl-11-chloro-1,8-dioxa-3-aza-dibenzo[e,h]azulene (Table 2, compounds 18–22).

TABLE 2

Compounds of structure I

| Comp. | X | Y | Z | R[1] | MS (m/z) | $^1$H NMR(ppm, CDCl$_3$) |
|---|---|---|---|---|---|---|
| 14 | S | H | H | CH$_2$OH | 304.2 (MNa$^+$) | 5.30(s, 2H); 7.35–7.88(m, 8H) |
| 15 | S | H | H | (CH$_2$)$_3$OH | 310.0 (MH$^+$) | |
| 16 | O | H | H | (CH$_2$)$_3$OH | 294.0 (MH$^+$) | |
| 17 | S | H | H | CH$_2$Br | | 4.62(s, 2H); 7.38–8.10(m, 8H) |
| 18 | O | H | H | CH$_2$Br | | 4.57(s, 2H); 7.16–7.76(m, 8H) |
| 19 | S | 5-Cl | H | CH$_2$Br | | 4.62(s, 2H); 7.35–7.88(m, 7H) |
| 20 | S | H | 11-Cl | CH$_2$Br | 379.9 (MH$^+$) | 4.61(s, 2H); 7.33–7.85(m, 7H) |
| 21 | O | 5-Cl | H | CH$_2$Br | | 4.59(s, 2H); 7.20–7.78(m, 7H) |
| 22 | O | H | 11-Cl | CH$_2$Br | | 4.59(s, 2H); 7.16–7.75(m, 7H) |

EXAMPLE 7 a) Dimethyl-[2-(1-oxa-8-thia-3-aza-dibenzo[e,h]azulene-2-ylmethoxy)-ethyl]-amine (I; X=S, Y=Z=H, R$_1$=(CH$_3$)$_2$N(CH$_2$)$_2$OCH$_2$)

To a solution of 2-dimethylaminoethylchloride-hydrochloride (0.718 g, 4.984 mmole) in 50% sodium hydroxide (3.9 ml), a catalytic amount of benzyltriethylammonium chloride and a solution of alcohol 14 (0.100 g, 0.356 mmole) in toluene (15 ml) were added. The reaction mixture was heated under reflux and vigorous stirring for 4 hours. Then it was cooled to room temperature, diluted with water and extracted with dichloromethane. The organic extract was dried over anhydrous Na$_2$SO$_4$ and evaporated. After purifying by chromatography on a column, an oily product was isolated.
MS (m/z; MeOH): 353.2 MH$^+$.

b) Dimethyl-[3-(1-oxa-8-thia-3-aza-dibenzo[e,h]azulene-2-ylmethoxy)-propyl]-amine (I; X=S, Y=Z=H, R$_1$=(CH$_3$)$_2$N(CH$_2$)$_3$OCH$_2$)

By the reaction of alcohol 14 (0.070 g, 0.249 mmole) and 3-dimethylaminopropylchloride-hydrochloride (0.551 g, 3.486 mmole), a colourless oily product was obtained.
MS (m/z; MeOH): 367.2 MH$^+$, 389.2 MNa$^+$.

EXAMPLE 8 a) Dimethyl-{2-[3-(1-oxa-8-thia-3-aza-dibenzo[e,h]azulene-2-yl)-propoxy]-ethyl}-amine (I; X=S, Y=Z=H, R$_1$=(CH$_3$)$_2$N(CH$_2$O(CH$_2$)$_3$)

To a solution of 2-dimethylaminoethylchloride-hydrochloride (1.010 g, 7.014 mmole) in 50% sodium hydroxide (6.2 ml), a catalytic amount of benzyltriethylammoniun chloride and a solution of alcohol 15 (0.155 g, 0.501 mmole) in toluene (20 ml) were added. The reaction mixture was heated under reflux and vigorous stirring for 4 hours. Then it was cooled to room temperature, diluted with water and extracted with dichloromethane. The organic extract was dried over anhydrous Na$_2$SO$_4$ and evaporated. After purifying by chromatography on a column, a yellow oily product was isolated.
MS (m/z; MeOH): 380.9 MH$^+$, 402.9 MNa$^+$.

b) Dimethyl-{3-[3-(1-oxa-8-thia-3-aza-dibenzo[e,h]azulene-2-yl)-propoxy]-propyl}-amine (I; X=S, Y=Z=H, R$_1$=(CH$_3$)$_2$N(CH$_2$)$_3$O(CH$_2$)$_3$)

By the reaction of alcohol 15 (0.155 g, 0.501 mmole) and 3-dimethylaminopropylchloride-hydrochloride (1.11 g, 7.014 mmole), a yellow oily product was obtained.
MS (m/z; MeOH): 395.1 MH$^+$.

EXAMPLE 9 a) {2-[3-(1,8-Dioxa-3-aza-dibenzo[e,h]azulene-2-yl)-propoxy]-ethyl}-dimethylamine (I; X=O, Y=Z=H, R$_1$=(CH$_3$)$_2$N(CH$_2$)$_2$O(CH$_2$)$_3$)

To a solution of 2-dimethylaminoethylchloride-hydrochloride (0.653 g, 4.536 mmole) in 50% sodium hydroxide (4.0 ml), a catalytic amount of benzyltriethylammoniun chloride and a solution of alcohol 16 (0.095 g, 0.324 mmole) in toluene (15 ml) were added. The reaction mixture was heated under reflux and vigorous stirring for 4 hours. Then it was cooled to room temperature, diluted with water and extracted with dichloromethane. The organic extract was dried over anhydrous Na$_2$SO$_4$ and evaporated. After purifying by chromatography on a column, a yellow oily product was isolated.
MS (m/z; MeOH): 365.0 MH$^+$, 386.9 MNa$^+$.

b) {3-[3-(1,8-Dioxa-3-aza-dibenzo[e,h]azulene-2-yl)-propoxy]-propyl}-dimethylamine (I; X=O, Y=Z=H, R$_1$=(CH$_3$)$_2$N(CHd$_3$O(CH$_2$)$_3$)

By the reaction of alcohol 16 (0.095 g, 0.324 mmole) and 3-dimethylaminopropylchloride-hydrochloride (0.720 g, 4.536 mmole), a yellow oily product was obtained.
MS (m/z; MeOH): 379.2 MH$^+$.

EXAMPLE 10 a) Dimethyl-[2-(1-oxa-8-thia-3-aza-dibenzo[e,h]azulene-2-ylmethoxy)-ethyl]-amine (I; X=S, Y=Z=H, R$_1$=(CH$_3$)$_2$N(CH$_2$)$_2$OCH$_2$)

To a solution of 2-dimethylaminoethanol (0.127 g, 1.425 mmole) in 50% sodium hydroxide (2.5 ml), a solution of bromide 17 (0.070 g, 0.204 mmole) in toluene (12 ml) was added. The reaction mixture was heated under reflux and vigorous stirring for 4 hours. Then it was cooled to room temperature, diluted with water and extracted with dichloromethane. The organic extract was dried over anhydrous Na$_2$SO$_4$ and evaporated. After purifying by chromatography on a column, a yellow oily product was isolated.
MS (m/z; MeOH): 353.0 MH$^+$, 374.9 MNa$^+$.

b) Dimethyl-[3-(1-oxa-8-thia-3-aza-dibenzo[e,h]azulene-2-ylmethoxy)-propyl]-amine (I; X=S, Y=Z=H, R$_1$=(CH$_3$)$_2$N(CH$_2$)$_3$OCH$_2$)

By the reaction of bromide 17 and 3-dimethylaminopropane-1-ol, a yellow oily product was obtained.
MS (m/z; MeOH): 367.3 MH$^+$, 389.3 MNa$^+$.

EXAMPLE 11 a) [2-(1,8-Dioxa-3-aza-dibenzo[e,h]azulene-2-ylmethoxy)-ethyl]-dimethylamine (I; X=O, Y=Z=H, R$_1$=(CH$_3$)$_2$N(CH$_2$)$_2$OCH$_2$)

To a solution of 2-dimethylaminoethanol (0.190 g, 2.134 mmole) in 50% sodium hydroxide (3.7 ml), a solution of bromide 18 (0.100 g, 0.305 mmole) in toluene (15 ml) was added. The reaction mixture was heated under reflux and vigorous stirring for 4 hours. Then it was cooled to room temperature, diluted with water and extracted with dichloromethane. The organic extract was dried over anhydrous Na$_2$SO$_4$ and evaporated. After purifying by chromatography on a column a yellow oily product was isolated;
MS (m/z; MeOH): 337.2 MH$^+$, 359.1 MNa$^+$.

b) [3-(1,8-Dioxa-3-aza-dibenzo[e,h]azulene-2-ylmethoxy)-propyl]-dimethylamine (I; X=O, Y=Z=H, R$_1$=(CH$_3$)$_2$N(CH$_2$)$_3$OCH$_2$)

By the reaction of bromide 18 and 3-dimethylaminopropane-1-ol a yellow oily product was obtained.
MS (m/z; MeOH): 351.3 MH$^+$, 373.3 MNa$^+$.

EXAMPLE 12 a) 2-(5-Chloro-1-oxa-8-thia-3-aza-dibenzo[e,h]azulene-2-ylmethoxy)-ethyl]-dimethylamine (I; X=S, Y=5-Cl, Z=H, $R_1=(CH_3)_2N(CH_2)_2OCH_2$)

To a solution of 2-dimethylaminoethanol (0.122 g, 1.370 nmmole) in 50% sodium hydroxide (2.4 ml), a solution of bromide 19 (0.074 g, 0.196 mmole) in toluene (12 ml) was added. The reaction mixture was heated under reflux and vigorous stirring for 4 hours. Then it was cooled to room temperature, diluted with water and extracted with dichloromethane. The organic extract was dried over anhydrous $Na_2SO_4$ and evaporated. After purifying by chromatography on a column, a yellow oily product was isolated.

MS (m/z; MeOH): 386.9 $MH^+$.

b) [3-(5-Chloro-1-oxa-8-thia-3-aza-dibenzo[e,h]azulene-2-ylmethoxy)-propyl]-dimethylamine (I; X=S, Y=5-Cl, Z=H, $R_1=(CH_3)_2N(CH_2)_3OCH_2$)

By the reaction of bromide 19 and 3-dimethylaminopropane-1-ol, a yellow oily product was obtained.

MS (m/z; MeOH): 403.1 $MH^+$.

c) [2-(11-Chloro-1-oxa-8-thia-3-aza-dibenzo[e,h]azulene-2-ylmethoxy)-ethyl]-dimethylamine (I; X=S, Y=H, Z=11-Cl, $R_1=(CH_3)_2N(CH_2)_2OCH_2$)

By the reaction of bromide 20 and 2-dimethylaminoethanol, a yellow oily product was obtained.

MS (m/z; MeOH): 387.0 $MH^+$.

EXAMPLE 13 a) [2-(5-Chloro-1,8-dioxa-3-aza-dibenzo[e,h]azulene-2-ylmethoxy)-ethyl]-dimethylamine (I; X=O, Y=5-Cl, Z=H, $R^1=(CH_3)_2N(CH_2)_2OCH_2$)

To a solution of 2-dimethylaminoethanol (0.112 g, 1.253 mmole) in 50% sodium hydroxide (2.2 ml), a solution of bromide 21 (0.065 g, 0.179 mmole) in toluene (10 ml) was added. The reaction mixture was heated under reflux and vigorous stirring for 4 hours. Then it was cooled to room temperature, diluted with water and extracted with dichloromethane. The organic extract was dried over anhydrous $Na_2SO_4$ and evaporated. After purifying by chromatography on a column, a yellow oily product was isolated.

MS (m/z; MeOH): 373.0 $MH^+$, 395.0 $MNa^+$.

b) [3-(5-Chloro-1,8-dioxa-3-aza-dibenzo[e,h]azulene-2-ylmethoxy)-propyl]-dimethylamine (I; X=O, Y=5-Cl, Z=H, $R_1=(CH_3)_2N(CH_2)_3OCH_2$)

By the reaction of bromide 21 and 3-dimethylaminopropane-1-ol, a yellow oily product was obtained.

MS (m/z; MeOH): 387.0 $MH^+$, 409.0 $MNa^+$.

c) [2-(11-Chloro-1,8-dioxa-3-aza-dibenzo[e,h]azulene-2-ylmethoxy)-ethyl]-dimethylamine (I; X=O, Y=H, Z=11-Cl, $R_1=(CH_3)_2N(CH_2)_2O(CH_2)$)

By the reaction of bromide 22 and 2-dimethylaminoethanol, a yellow oily product was obtained;

MS (m/z; MeOH): 373.1 $MH^+$, 395.1 $MNa^+$.

Preparation of the Starting Compounds

Process A

Dibenzo[b,f]thiepin-10,11-dione monooxime

11H-Dibenzo[b,f]thiepin-10-one (2.0 g, 8.8 mmole) was dissolved under stirring and heating to 75° C. in 3 M HCl in ethanol (36.4 ml). $NaNO_2$ (0.818 g, 11.86 mmole) was dissolved in a minimum amount of water and ethanol (1 ml) and the prepared solution was added to an ethanolic solution of HCl. The reaction mixture was heated for 2.5 hours and then cooled and neutralized with a 10% NaOH solution (pH~7–8). The solvent was partly evaporated and the precipitated product (green crystals) was filtered and washed with water.

According to the same process, starting from 11H-dibenzo[b,f]oxepin-10-one there was prepared dibenzo[b,f]oxepin-10,11-dione monooxime.

Process B

11-Amino-11H-dibenzo[b,f]thiepin-10-one-hydrochloride

To a solution of dibenzo[b,f]thiepin-10,11-dione monooxime (2.06 g, 8.078 mmole) in acetic acid (25.8 ml) cooled to 0° C., zinc (0.792 g, 12.1 mmole) was added. The reaction mixture was stirred for 30 minutes at the same temperature, whereupon the precipitate was filtered and acetic acid was evaporated to a dry residue. The obtained oily product was dissolved in a minimum amount of ethanol, then it was cooled to ° C. and acidified with HCl at this temperature, whereat a product was precipitated, which was subsequently filtered and washed with ether.

According to the same process, starting from dibenzo[b,f]oxepin-10,11-dione monooxime there was prepared 11-amino-11H-dibenzo[b,f]oxepin-10-one-hydrochloride.

Process C

N-(11-Oxo-10,11-dihydro-dibenzo[b,f]thiepin-10-yl)-formamide (III; X=S, Y=Z=H, A=NH, $R^1$=H)

To a suspension of formic acid (27.2 µl; 0.721 mmole) and dichloromethane (5 ml) cooled to 0° C. under a stream of argon, a solution of 11-amino-11H-dibenzo[b,f]thiepin-10-one-hydrochloride (0.200 g; 0.721 mmole) in dichloromethane (10 ml) and triethylamine (50 µl; 0.357 mmole) and the catalysts 1-hydroxybenzotriazole (0.195 g; 1.442 mmole) and 1-(3-dimethylaminopropyl)-3-ethyl-carbodiimide hydrochloride (0.580 g; 3.028 mmole) were added. The reaction mixture was stirred at room temperature for 24 hours. After the completion of the reaction, the solvent was evaporated, water was added and it was extracted with ethyl acetate. The organic extract was dried over anhydrous $Na_2SO_4$ and evaporated. After purifying by chromatography on a column, a white solid product was isolated.

According to the same process, starting from 11-amino-11H-dibenzo[b,f]oxepin-10-one-hydrochloride there was prepared N-(11-oxo-10,11-dihydro-dibenzo[b,f]oxepin-10-yl)-formamide (III; X=S, Y=Z=H, A=NH, $R^1$=H).

Process D

N-(11-oxo-10,11-dihydro-dibenzo[b,f]thiepin-10-yl)-succinamic acid ethyl ester (III; X=S, Y=Z=H, A=NH, $R^1=(CH_2)_2CO_2Et$)

To a solution of 11-amino-11H-dibenzo[b,f]thiepin-10-one-hydrochloride (0.159 g, 0.540 mmole) in pyridine (640

μl) cooled to 0° C., a solution of ethyl-succinyl-chloride (0.098 g, 0.594 mmole) in chloroform (220 μL) was added. The reaction mixture was stirred for another 2.5 hours at room temperature, the solvents were evaporated to a dry residue, water was added and it was extracted with ethyl acetate. The organic extract was dried over anhydrous $Na_2SO_4$ and evaporated. After purifying by chromatography on a column, a yellow solid product was isolated.

According to the same process, starting from 11-amino-11H-dibenzo[b,f]oxepin-10-one hydrochloride there was prepared N-(11-oxo-10,11-dihydro-dibenzo[b,f]-oxepin-10-yl)-succinamic acid ethyl ester (III; X=O, Y=Z=H, A=NH, $R^1$=$(CH_2)_2CO_2Et$).

Process E

11-Oxo-10,11-dihydro-dibenzo[b,f]thiepin-10-yl acetic acid ester (III, X=S, Y=Z=H, A=O, $R^1$=$CH_3$)

To a suspension of a plumbic (IV) acetate (3.9 g, 8.8 mmole) in acetic acid, a solution of 11H-dibenzo[b,f]thiepin-10-one (2.0 g, 8.8 mmole) in acetic acid (5 ml) was added. The reaction mixture was heated under reflux for some hours, whereupon the acetic acid was filtered off by Hickmann distillation apparatus and then water was added thereto and it was extracted with ethyl acetate. The organic extract was washed with a saturated $NaHCO_3$ solution and water, dried over anhydrous $Na_2SO_4$ and evaporated to a dry residue. After purifying by chromatography on a column, a yellow solid product was isolated.

According to the same process starting from:
11H-dibenzo[b,f]oxepin-10-one;
8-chloro-11H-dibenzo[b,f]thiepin-10-one;
8-chloro-11H-dibenzo[b,f]oxepin-10-one, there were prepared the compounds:
11-oxo-10,11-dihydro-dibenzo[b,f]oxepin-10-yl acetic acid ester (III; X=O, Y=Z=H, A=O, $R^1$=$CH_3$);
2-chloro-11-oxo-10,11-dihydro-dibenzo[b,f]thiepin-10-yl acetic acid ester (III; X=S, Y=H, Z=2-Cl, A=O, $R^1$=$CH_3$);
2-chloro-11-oxo-10,11-dihydro-dibenzo[b,f]oxepin-10-yl acetic acid ester (III; X=O, Y=H, Z=2-Cl, A=O, $R^1$=$CH_3$).

TABLE 3

Compounds of structure III

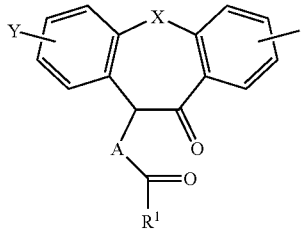

| X | Y | Z | A | $R^1$ | MS (m/z) | $^1$H NMR (ppm, $CDCl_3$) |
|---|---|---|---|---|---|---|
| S | H | H | NH | H | 292.0 ($MNa^+$) | 6.72–6.74 (d, 1H); 7.19–7.69 (m, 8H); 8.26–8.29 (d, 1H); 8.47 (s, 1H) |
| O | H | H | NH | H | 276.0 ($MNa^+$) | 6.33–6.35 (d, 1H); 7.16–7.62 (m, 8H); 8.07–8.10 (m, 1H); 8.54 (s, 1H) |
| S | H | H | NH | $(CH_2)_2CO_2Et$ | 370.2 ($MH^+$) | 1.23–1.28 (t, 3H); 2.69–2.76 (m, 4H); 4.13–4.20 (q, 2H); 6.66 (d, 1H); 7.19–7.67 (m, 8H); 8.26–8.29 (dd, 1H) |
| O | H | H | NH | $(CH_2)_2CO_2Et$ | 354.1 ($MH^+$) |  |
| S | H | H | O | $CH_3$ | 307.1 ($MNa^+$) | 2.36 (s, 3H); 7.07 (s, 1H); 7.25–8.25 (m, 8H) |
| O | H | H | O | $CH_3$ |  | 2.38 (s, 3H); 6.67 (s, 1H); 7.19–8.09 (m, 8H) |
| S | H | 2-Cl | O | $CH_3$ |  | 2.36 (s, 3H); 7.08 (s, 1H); 7.26–8.25 (m, 7H) |
| O | H | 2-Cl | O | $CH_3$ | 325.1 ($MNa^+$) | 2.38–2.39 (d, 3H); 6.73–6.74 (d, 1H); 7.12–8.08 (m, 7H) |

The invention claimed is:

1. A compound of the formula I

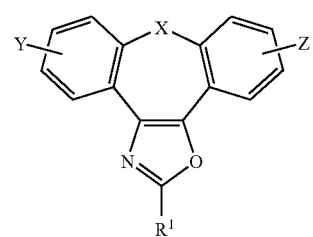

wherein

X is O, S, S(=O), S(=O)$_2$, or $NR^a$, wherein $R^a$ is hydrogen or a protecting group;

Y and Z are each independently hydrogen, halogen, $C_1$–$C_4$ alkyl, $C_2$–$C_4$ alkenyl, $C_2$–$C_4$ alkynyl, halo-$C_1$–$C_4$ alkyl, hydroxy, $C_1$–$C_4$ alkoxy, trifluoromethyl, trifluoromethoxy, $C_1$–$C_4$ alkanoyl, amino, amino-$C_1$–$C_4$ alkyl, N—($C_1$–$C_4$alkyl)amino, N,N-di($C_1$–$C_4$-alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano or nitro;

$R^1$ is hydrogen, $C_1$–$C_7$ alkyl, CHO, $(CH_2)_2COOH$, $(CH_2)_2CO_2Et$, $(CH_2)_mL$, wherein m is 1 or 3 and L is OH or Br;

or a substituent of the formula II

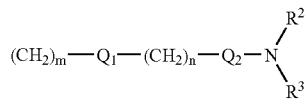

wherein
R² and R³ are each independently hydrogen, C₁–C₄ alkyl, aryl or R² and R³ taken together with the nitrogen atom to which they are attached are an optionally substituted heterocycle or heteroaryl;
m is integer from 1 to 3;
n is integer from 0 to 3;
Q₁ and Q₂ are each independently oxygen, sulphur

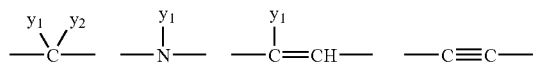

wherein
y₁ and y₂ are each independently hydrogen, halogen, C₁–C₄ alkyl or aryl, hydroxy, C₁–C₄ alkoxy, C₁–C₄ alkanoyl, thiol, C₁–C₄ alkylthio, sulfonyl, C₁–C₄ alkylsulfonyl, sulfinyl, C₁–C₄ alkylsulfinyl, cyano, nitro or y₁ and y₂ taken together with the carbon or nitrogen atom to which they are attached form a carbonyl group or an imino group;
and a pharmacologically acceptable salt or solvate salt thereof,
wherein an optionally substituted heteroaryl or heterocycle is a heteroaryl or heterocyclic group, which is substituted with one or two substituents, selected from the group consisting of halogen, C₁–C₄ alkyl, cyano, nitro, hydroxy, C₁–C₄ alkoxy, thiol, C₁–C₄ alkylthio, amino, N—(C₁–C₄) alkylamino, N,N-di(C₁–C₄-alkyl)-amino, sulfonyl, C₁–C₄ alkylsulfonyl, sulfinyl, and C₁–C₄ alkylsulfinyl.

2. The compound according to claim 1, wherein X is S or O.

3. The compound according to claim 2, wherein Y and Z are each independently H, or Cl.

4. The compound according to claim 3, wherein R¹ is H, CH₃, CHO, (CH₂)₂COOH, or (CH₂)₂CO₂Et.

5. The compound according to claim 3, wherein R¹ is (CH₂)ₘL.

6. The compound according to claim 5, wherein m is 1 or 3.

7. The compound according to claim 6, wherein L is OH or Br.

8. The compound according to claim 3, wherein R¹ is a substituent of the formula II.

9. The compound according to claim 8, wherein m 1 or 3 n is 1 or 2, Q₁ is O, Q₂ is CH₂ and R¹ and R² are each CH₃.

10. The compound according to claim 4 selected from the group consisting of:
1-oxa-8-thia-3-aza-dibenzo[e,h]azulene;
1,8-dioxa-3-aza-dibenzo[e,h]azulene;
3-(1-oxa-8-thia-3-aza-dibenzo[e,h]azulene-2-yl)-propionic acid ethyl ester;
3-(1,8-dioxa-3-aza-dibenzo[e,h]azulene-2-yl)-propionic acid ethyl ester;
2-methyl-1-oxa-8-thia-3-aza-dibenzo[e,h]azulene;
2-methyl-1,8-dioxa-3-aza-dibenzo[e,h]azulene;
11-chloro-2-methyl-1-oxa-8-thia-3-aza-dibenzo[e,h]azulene;
5-chloro-2-methyl-1-oxa-8-thia-3-aza-dibenzo[e,h]azulene;
11-chloro-2-methyl-1,8-dioxa-3-aza-dibenzo[e,h]azulene;
5-chloro-2-methyl-1,8-dioxa-3-aza-dibenzo[e,h]azulene;
1-oxa-8-thia-3-aza-dibenzo[e,h]azulene-2-carbaldehyde;
3-(1-oxa-8-thia-3-aza-dibenzo[e,h]azulene-2-yl)-propionic acid; and
3-(1,8-dioxa-3-aza-dibenzo[e,h]azulene-2-yl)-propionic acid.

11. The compound according to claim 7 selected from the group consisting of:
(1-oxa-8-thia-3-aza-dibenzo[e,h]azulene-2-yl)-methanol;
3-(1-oxa-8-thia-3-aza-dibenzo[e,h]azulene-2-yl)-propane-1-ol;
3-(1,8-dioxa-3-aza-dibenzo[e,h]azulene-2-yl)-propane-1-ol;
2-bromomethyl-1-oxa-8-thia-3-aza-dibenzo[e,h]azulene;
2-bromomethyl-1,8-dioxa-3-aza-dibenzo[e,h]azulene;
2-bromomethyl-5-chloro-1-oxa-8-thia-3-aza-dibenzo[e,h]azulene;
2-bromomethyl-11-chloro-1-oxa-8-thia-3-aza-dibenzo[e,h]azulene;
2-bromomethyl-5-chloro-1,8-dioxa-3-aza-dibenzo[e,h]azulene; and
2-bromomethyl-11-chloro-1,8-dioxa-3-aza-dibenzo[e,h]azulene.

12. The compound according to claim 9 selected from the group consisting of:
dimethyl-[2-(1-oxa-8-thia-3-aza-dibenzo[e,h]azulene-2-ylmethoxy)-ethyl]-amine;
dimethyl-[3-(1-oxa-8-thia-3-aza-dibenzo[e,h]azulene-2-ylmethoxy)-propyl]-amine;
dimethyl-{2-[3-(1-oxa-8-thia-3-aza-dibenzo[e,h]azulene-2-yl)-propoxy]-ethyl}-amine; dimethyl-{3-[3-(1-oxa-8-thia-3-aza-dibenzo[e,h]azulene-2-yl)-propoxy]-propyl}-amine;
{2-[3-(1,8-dioxa-3-aza-dibenzo[e,h]azulene-2-yl)-propoxy]-ethyl}-dimethylamine;
{3-[3-(1,8-dioxa-3-aza-dibenzo[e,h]azulene-2-yl)-propoxy]-propyl}-dimethylamine;
[2-(1,8-dioxa-3-aza-dibenzo[e,h]azulene-2-ylmethoxy)-ethyl]-dimethylamine;
[3-(1,8-dioxa-3-aza-dibenzo[e,h]azulene-2-ylmethoxy)-propyl]-dimethylamine;
2-(5-chloro-1-oxa-8-thia-3-aza-dibenzo[e,h]azulene-2-ylmethoxy)-ethyl]-dimethylamine;
[3-(5-chloro-1-oxa-8-thia-3-aza-dibenzo[e,h]azulene-2-ylmethoxy)-propyl]-dimethylamine;
[2-(1-chloro-1-oxa-8-thia-3-aza-dibenzo[e,h]azulene-2-ylmethoxy)-ethyl]-dimethylamine;
[3-(11-chloro-1-oxa-8-thia-3-aza-dibenzo[e,h]azulene-2-ylmethoxy)-propyl]-dimethylamine;
[2-(5-chloro-1,8-dioxa-3-aza-dibenzo[e,h]azulene-2-ylmethoxy)-ethyl]-dimethylamine;
[3-(5-chloro-1,8-dioxa-3-aza-dibenzo[e,h]azulene-2-ylmethoxy)-propyl]-dimethylamine;
[2-(11-chloro-1,8-dioxa-3-aza-dibenzo[e,h]azulene-2-ylmethoxy)-ethyl]-dimethylamine;
[3-(11-chloro-1,8-dioxa-3-aza-dibenzo[e,h]azulene-2-ylmethoxy)-propyl]-dimethylamine; and a pharmacologically acceptable salt thereof.

13. A process for the preparation of a compound of the formula I

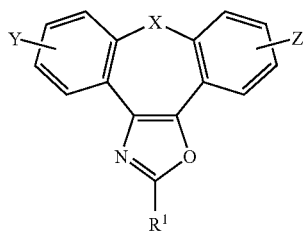

wherein
X is O, S, S(=O), S(=O)$_2$, or NR$^a$, wherein R$^a$ is hydrogen or a protecting group;
Y and Z are each independently hydrogen, halogen, $C_1$–$C_4$ alkyl, $C_2$–$C_4$ alkenyl, $C_2$–$C_4$ alkynyl, halo-$C_1$–$C_4$ alkyl, hydroxy, $C_1$–$C_4$ alkoxy, trifluoromethyl, trifluoromethoxy, $C_1$–$C_4$ alkanoyl, amino, amino-$C_1$–$C_4$ alkyl, N—($C_1$–$C_4$–alkyl)amino, N,N-di($C_1$–$C_4$-alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano or nitro;
R$^1$ is hydrogen, $C_1$–$C_7$ alkyl, CHO, (CH$_2$)$_2$COOH, (CH$_2$)$_2$CO$_2$Et, (CH$_2$)$_m$L, wherein m is 1 or 3 and L at is OH or Br;
or a sub substituent of the formula II

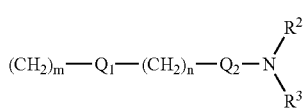

wherein
R$^2$ and R$^3$ are each independently hydrogen, $C_1$–$C_4$ alkyl, aryl or R$^2$ and R$^3$ taken together with the nitrogen atom to which they are attached are an optionally substituted heterocycle or heteroaryl;
m is integer from 1 to 3;
n is integer from 0 to 3,
Q$_1$ and Q$_2$ represent, independently from each other, are each independently oxygen, sulphur,

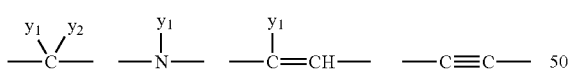

wherein the substituents
y$_1$ and y$_2$ are each independently hydrogen, halogen, $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, nitro or y$_1$ and y$_2$ taken together with the carbon or nitrogen atom to which they are attached form a carbonyl group or an imino group;
and a pharmacologically acceptable salt or solvate thereof,
wherein an optionally substituted heteroaryl or heterocycle is a heteroaryl or heterocyclic group, which is substituted with one or two substituents, selected from the group consisting of halogen, $C_1$–$C_4$ alkyl, cyano, nitro, hydroxy, $C_1$–$C_4$ alkoxy, thiol, $C_1$–$C_4$ alkylthio, amino, N-($C_1$–$C_4$) alkylamino, N,N-di($C_1$–$C_4$-alkyl)-amino, sulfonyl, $C_1$–$C_4$ alkylsulfonyl, sulfinyl, and $C_1$–$C_4$ alkylsulfinyl comprising one of the following steps a) through e)

a) for a compound of the formula I, cyclizing a compound of the formula III

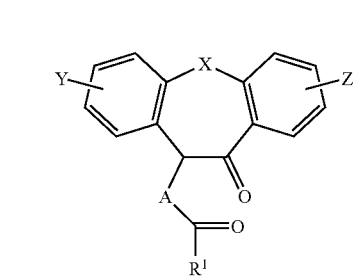

wherein A of is —O— or —NH—;
b) for a compound of the formula I, wherein Q$_1$ is —O—, reacting an alcohol of the formula IV:

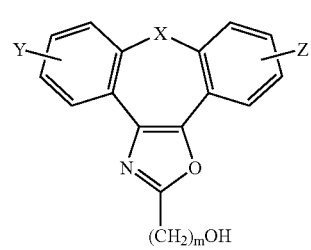

with a compound of the formula V:

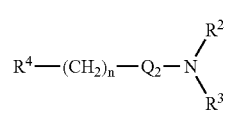

wherein R$^4$ is a leaving group;
c) for a compound of the formula I, wherein Q$_1$ is —O—, —NH—, —S— or —C≡C—,
reacting a compound of the formula IVa

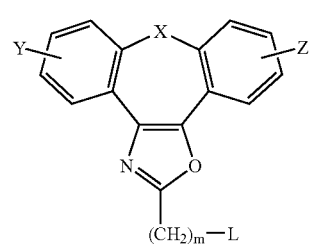

wherein L is a leaving group,
with a compound of the formula Va

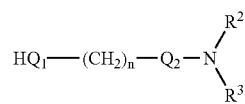

d) for a compound of the formula I, wherein Q$_1$ is —O—, —NH— or —S—, reacting a compound of the formula IVb

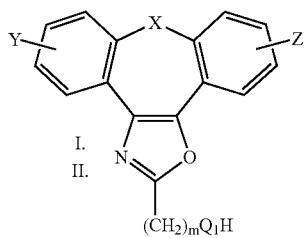
I.
II.
IVb with a compound of the formula V, wherein $R^4$ is a leaving group; or e) for a compound of the formula I, wherein $Q_1$ is —C≡C—, reacting a compound of the formula IVb, wherein $Q_1$ is a carbonyl, with a phosphorous ylide.

14. A method of treating a pathological condition or disease induced by an excessive unregulated production of a cytokine or inflammation mediator comprising administering to a subject an effective amount of a compound according to claim 8 perorally, parenterally or locally.

* * * * *